United States Patent [19]

Mylvaganam et al.

[11] Patent Number: 4,945,276
[45] Date of Patent: Jul. 31, 1990

[54] TRANSDUCER FOR ARRANGING IN A FLUID, PARTICULARLY FOR THE MEASUREMENT OF THE FLOW-VELOCITY OF A FLUID IN A PIPE, BY TRANSMITTING/RECEIVING SONIC PULSES

[75] Inventors: Kanagasaba Mylvaganam, Skjoldtun; Erling Hammer, Mjlkeraen, both of Norway

[73] Assignee: Den Norske Stats Oljeselskap A.S., Stavanger, Norway

[21] Appl. No.: 312,587

[22] PCT Filed: Apr. 20, 1988

[86] PCT No.: PCT/NO88/00029

§ 371 Date: Feb. 3, 1989

§ 102(e) Date: Feb. 3, 1989

[87] PCT Pub. No.: WO88/08539

PCT Pub. Date: Nov. 3, 1988

[30] Foreign Application Priority Data

Apr. 24, 1987 [NO] Norway .................. 871700

[51] Int. Cl.$^5$ .................................... H01L 41/08
[52] U.S. Cl. .................................... 310/326; 310/334; 73/290 V; 73/644; 73/861.18
[58] Field of Search ............... 310/324, 326, 327, 338, 310/334–337; 73/644, 861.18, 290 V

[56] References Cited

U.S. PATENT DOCUMENTS

| 3,204,458 | 9/1965 | Gillen | 73/194 |
|---|---|---|---|
| 3,218,852 | 11/1965 | Scarpa et al. | 73/194 |
| 3,349,259 | 10/1967 | Kistler | 310/338 |
| 3,469,445 | 9/1969 | Moffatt | 73/194 |
| 3,555,311 | 1/1971 | Weber | 310/326 X |
| 3,801,838 | 4/1974 | Kistler | 310/338 |
| 3,834,233 | 9/1974 | Willis et al. | 73/290 V |
| 3,835,704 | 9/1974 | Elazar et al. | 73/194 A |
| 3,898,840 | 8/1975 | McElroy | 310/326 X |
| 4,326,274 | 4/1982 | Hotta et al. | 367/118 |
| 4,359,659 | 11/1982 | Phillips | 310/326 X |
| 4,397,193 | 8/1983 | Ryan et al. | 73/861.28 |
| 4,410,825 | 10/1983 | Lobastov | 310/338 X |
| 4,556,814 | 12/1985 | Ito et al. | 310/334 |
| 4,578,611 | 3/1986 | Sadler | 310/338 |
| 4,698,541 | 10/1987 | Cohen | 310/326 |
| 4,700,575 | 10/1987 | Geithman et al. | 310/326 X |
| 4,712,036 | 12/1987 | Gurich | 310/338 X |

FOREIGN PATENT DOCUMENTS

| 147718B | 11/1984 | Denmark . |
| 0178346 | 4/1986 | European Pat. Off. . |
| 1773777 | 4/1972 | Fed. Rep. of Germany . |
| 896806 | 3/1945 | France . |
| 1530347 | 10/1978 | United Kingdom . |
| 1580720 | 12/1980 | United Kingdom . |

OTHER PUBLICATIONS

"Theoretical Analysis of the Basic Parameters of Ultrasonic Flowmeters", by N.I. Brazhnikov (Translated from Izmeritel'naya Tekhnika, No. 8, pp. 57–62, Aug., 1966.

Primary Examiner—Mark O. Budd
Attorney, Agent, or Firm—Foley & Lardner, Schwartz, Jeffery, Schwaab, Mack, Blumenthal & Evans

[57] ABSTRACT

A transducer for arranging in a fluid particularly for the measurement of the flow velocity of a fluid in a pipe by transmitting/receiving sonic pulses, is designed as a cupshaped metal body (5), whose base (2) as membrane (3) is assigned an electrode (4) on its inside, which is sealed off against the environment i.e. against the fluid, and whose cup wall is designed with an annulus (6) filled with a powerful damping material (8), for example epoxy, rubber or epoxy mixed with metal particles.

6 Claims, 1 Drawing Sheet

4,945,276

TRANSDUCER FOR ARRANGING IN A FLUID, PARTICULARLY FOR THE MEASUREMENT OF THE FLOW-VELOCITY OF A FLUID IN A PIPE, BY TRANSMITTING/RECEIVING SONIC PULSES

This invention relates to a transducer for arranging in a fluid for measuring the flow-velocity of a fluid in a pipe, by transmitting/receiving sonic pulses.

TECHNICAL FIELD

The invention is developed especially in connection with the need for and development of a transducer arrangement operating with ultra-sound, for measuring the flow velocity of a fluid in a pipe, comprising two transducers, mounted on their respective sides of the pipe, and directed obliquely in relation to the flow-direction, which alternately transmit and receive sonic pulses to and from each other, however, the invention is not restricted to this specific application, since the new transducer can also be utilized for other purposes, for instance for measuring the fluid level in a container. Hence, when specific conditions for development are described in the following, these are not to be considered as limiting, but merely represent a demonstration of the developmental basis from which progress has taken place. So, as mentioned, the new transducer is developed in connection with a transducer device for measuring the gas flow to a so-called flare in connection with facilities for exploration and production of hydrocarbons. In this connection there is a definite need to be able to cover a relatively large range of flow-velocity in an accurate manner, and at the same time there is a need for safety, particularly in the case of measuring in so-called danger areas.

BACKGROUND ART

The transducer devices which are known today operate with transducers which are mounted and dimensioned for relatively limited velocity ranges. The accuracy of measurement in such devices is not always completely satisfactory.

A particular aim of the present invention is to provide an electroacoustic transducer for application in gasses and liquids in potentially explosive areas where there is a demand for a reliable transducer embodiment which will be able to supply sufficient acoustic energy for various purposes.

DISCLOSURE OF INVENTION

In order to achieve this object, a transducer is suggested according to the invention, which transducer is is designed as a cup-shaped metal body having a base which forms a membrane is assigned an electrode on its inside which is sealed off from the environment that is, from the fluid, and the cup-wall of the body is designed with an annulus filled with a powerful damping material, for example epoxy, rubber or epoxy mixed with metal particles.

Such a cup-formed metal body can be formed, with regard to the utilization of the base as a membrane, by means of suitable machining, and the annulus can also be machined out in a suitable way without particular difficulty. The base designed as a membrane in the cup-formed metal body is connected with an electrode in the form of a piezo-electric driving element with suitable characteristics. The metal cup functions then as the one electrode, while the piezo-electric driving element's free end serves as the other electrode for electric excitation of the transducer.

The operational frequency of the transducer can be selected by choosing suitable dimensions for the piezo-electric driving element and for the thickness of the membrane. Transducers can thus cover both ordinary sonic frequencies and ultrasonic frequencies.

The new transducer is suitable for use in measuring the velocity of gasses and liquids, also in so-called danger areas (where a danger of explosion exists). A metal material for the cup-shaped body is chosen according to the demands which are made to transducers (environmental requirements). Titanium, steel, aluminium, carbon fiber and other materials can thus be used for the transducer cup.

The annulus can extend from the mounting side of the transducer and out to the same level as the membrane, but it can also extend from the end facing the environment.

The entire cup-formed body can be attached to a supporter on the mounting side in a hermetically sealing manner, so that the electric contacts will not be exposed to the environment wherein the transducer is to operate. This is naturally particularly advantageous if the transducer is used in an explosive environment.

The new transducer combines a high degree of efficiency with low ringing. These are characteristics which are normally incompatible. For example, with a transducer according to the invention, a transmitter efficiency degree of 50 dB re 1 Pa SPL/V and a Q-value $\sim$2.5, are achieved, which corresponds to a low after-vibration.

The membrane design which is utilized provides good coupling with a gas medium. A relatively large mass of metal will be situated at the edge of the membrane, in order to achieve the desired boundary conditions and to prevent too strong coupling to the housing or the rest of the cup. The coupling to the housing will cause after-ringing. This can be suppressed advantageously by means of the mentioned built-in damping material in the annulus.

BRIEF DESCRIPTION OF DRAWINGS

The invention will be more closely described with reference to the drawings where.

MODES OF CARRYING OUT THE INVENTION

Figure 1:
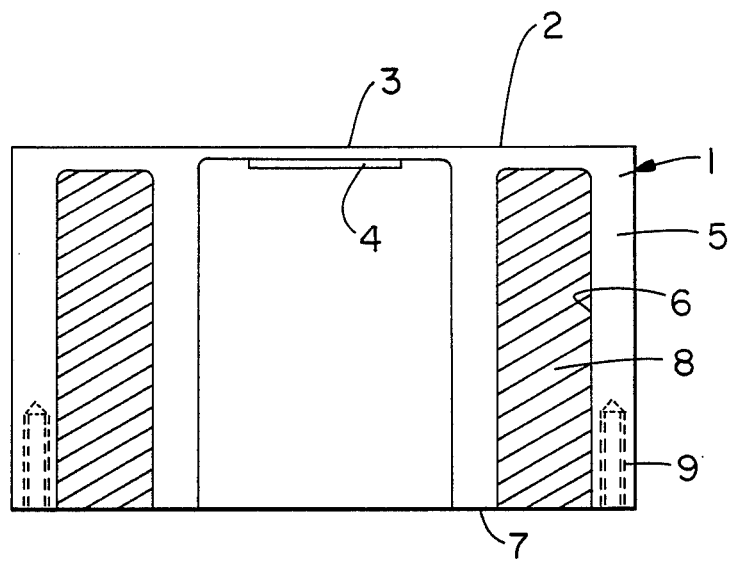
FIG. 1 show a possible, advantageous embodiment of the new transducer.

The transducer 1, shown in FIG. 1, is shown in section and is cup-formed. The base 2 of the cup is machined so that it forms a membrane 3. On the inside of this membrane 3 a suitable piezo-electric element 4 is mounted. The actual cup or housing 5 can then serve as one of the electrodes while the free end of the piezo-electric element 4 is utilized as the other electrode for electric excitation of the transducer.

As shown in FIG. 1, the side wall of the cup or housing 5 is machined so that an annulus 6 is produced. This annulus is so deep that it extends from the mounting side 7 of the transducer and all the way out to the level of the membrane 3. The annulus 6 is filled with a powerful damping material 8. Such a damping material can be, for example epoxy, rubber or epoxy incorporating metal particles.

The actual transducer housing 5 can be coupled, in a hermetically sealing manner, to a not shown supporter on the mounting side 7, where threaded bores 9 suitable for this purpose are indicated. By means of this simple method, known to anyone skilled in the art, of achieving tightly sealed connections, exposure of the electric contacts to the environment in which the transducer is to operate, can be prevented. This is naturally particularly advantageous in the case of the transducer being used in an explosive environment The operational frequency of the transducer can be determined by choosing suitable dimensions for the piezo-electric element 4 and the thickness of the metal membrane 3. The metal membrane's thickness can be determined by means of machining of the housing 5, i.e. its base 2. Thus, the transducer shown in FIG. 1 can be designed to cover both normal sonic frequencies and ultrasonic frequencies.

A metal material for the housing or cup 5 is chosen according to the demands made to transducers (environmental demands). Titanium, steel, aluminium, carbon fiber and other materials can thus be used.

It will be understood that the utilized membrane embodiment provides satisfactory coupling to a gas medium. At the edge of the membrane 3 there will be a relatively large mass of metal achieving the desired boundary conditions and preventing too strong coupling to the rest of the housing. The coupling to the housing will produce reverberation; this can be suppressed advantageously by means of the built-in damping material in the annulus 6.

Figure 2:
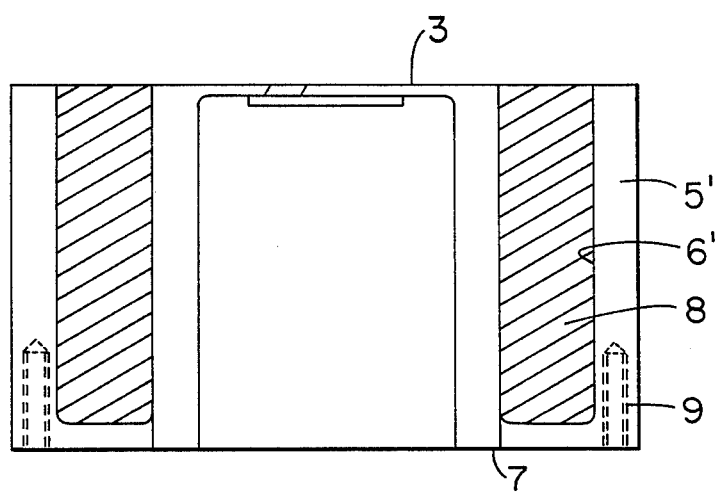
FIG. 2 shows another possible advantageous embodiment of the new transducer.
Figure 2:
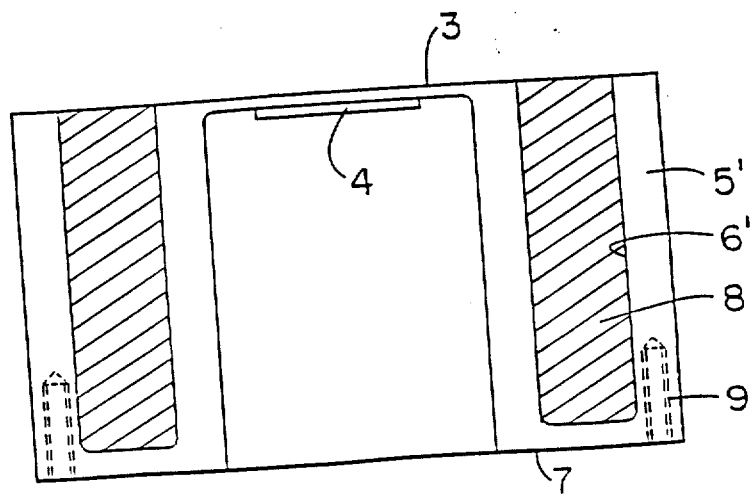

The embodiment in FIG. 2 corresponds almost totally with the embodiment in FIG. 1, the only difference being that the annulus 6' is machined out from the membrane side and not from the mounting side. The same reference numerals are therefore used as in FIG. 1, but with the addition of an index for the reference numerals 6' and 5' which indicate respectively the annulus and the cup-formed housing.

We claim:

1. A transducer for measurement of flow velocity of a fluid by transmitting and receiving sonic pulses, comprising:
    a one-piece cup-shaped housing, said housing having a base portion at a closed end thereof and a cylindrical cup-wall portion, thereby forming a hollow central cylindrical chamber;
    a membrane forming a central portion of said base portion, said membrane terminating adjacent said cylindrical cup-wall portion;
    an electrode centrally disposed on an inner side of said membrane so that a first side of said electrode is connected to said membrane, while a second side of said electrode communicates with said central cylindrical chamber;
    means for defining an annular chamber within said cylindrical cup-wall portion; and
    means, filling said annular chamber, for damping vibration in the cup-shaped housing.

2. The transducer according to claim 1, wherein said cup-shaped housing is formed of metal.

3. The transducer according to claim 1, wherein said damping means is formed of a material selected from the group consisting of epoxy, rubber and epoxy mixed with rubber particles.

4. The transducer according to claim 3, wherein said annular chamber is open toward said base portion.

5. The transducer according to claim 3, wherein said annular chamber is open toward a top portion of said cup-shaped housing.

6. The transducer according to claim 3, wherein said cup-shaped housing comprises titanium.

* * * * *

UNITED STATES PATENT AND TRADEMARK OFFICE
CERTIFICATE OF CORRECTION

PATENT NO. : 4,945,276

DATED : July 31, 1990

INVENTOR(S) : Kanaga Sabapathy Mylvaganam et al

It is certified that error appears in the above-identified patent and that said Letters Patent is hereby corrected as shown below:

On the title page, item [75] should read --Kanaga Sabapathy Mylvaganam, Nordås; Erling Hammer, Mjølkeråen, both of Norway--.

In the drawings, Fig. 2, should be deleted and replaced with the corrected Fig. 2, as shown on the attached page.

Column 1, line 14, "ultra-sound" should read --ultrasound--.

Column 1, line 44, "gasses" should read --gases--.

Column 1, line 52, delete "is".

Column 1, line 54, after "membrane" insert --to which--.

Column 2, line 9, "gasses" should read --gases--.

Column 2, line 11, "is-chosen" should read --is chosen--.

Column 2, line 32, "value_2.5" should read --value of 2.5--.

Signed and Sealed this

Sixth Day of July, 1993

*Attest:*

MICHAEL K. KIRK

*Attesting Officer*  *Acting Commissioner of Patents and Trademarks*